US012073927B2

(12) United States Patent
Stein et al.

(10) Patent No.: US 12,073,927 B2
(45) Date of Patent: Aug. 27, 2024

(54) SYSTEMS AND METHODS FOR REGULATION COMPLIANT COMPUTING

(71) Applicant: Shadowbox, Inc., Encinitas, CA (US)

(72) Inventors: Gregory Stein, Encinitas, CA (US); Jack Samatov, Encinitas, CA (US)

(73) Assignee: Shadowbox, Inc., Encinitas, CA (US)

( * ) Notice: Subject to any disclaimer, the term of this patent is extended or adjusted under 35 U.S.C. 154(b) by 748 days.

(21) Appl. No.: 17/279,500

(22) PCT Filed: Sep. 27, 2018

(86) PCT No.: PCT/US2018/053040
§ 371 (c)(1),
(2) Date: Mar. 24, 2021

(87) PCT Pub. No.: WO2020/068082
PCT Pub. Date: Apr. 2, 2020

(65) Prior Publication Data
US 2021/0397735 A1    Dec. 23, 2021

(51) Int. Cl.
*G16H 10/60* (2018.01)
*G06F 9/451* (2018.01)
*G06F 21/62* (2013.01)

(52) U.S. Cl.
CPC ............. *G16H 10/60* (2018.01); *G06F 9/451* (2018.02); *G06F 21/629* (2013.01)

(58) Field of Classification Search
None
See application file for complete search history.

(56) References Cited

U.S. PATENT DOCUMENTS

| 7,150,002 | B1 | 12/2006 | Anderson et al. |
| 7,669,141 | B1 | 2/2010 | Pegg |
| 7,827,494 | B1 | 11/2010 | Hedayatpour et al. |
| 9,858,166 | B1 | 1/2018 | Gong |
| 10,289,390 | B2 | 5/2019 | Samatov et al. |
| 10,380,568 | B1 * | 8/2019 | Rogers ............... G06Q 20/1235 |
| 10,652,279 | B1 * | 5/2020 | Blitz ....................... H04L 63/20 |
| 2005/0182655 | A1 | 8/2005 | Merzlak et al. |
| 2008/0021732 | A1 | 1/2008 | Richards et al. |
| 2009/0228716 | A1 | 9/2009 | Poston et al. |
| 2010/0161660 | A1 | 6/2010 | De Angelo |
| 2010/0198649 | A1 * | 8/2010 | Appleyard ......... G06Q 10/1097 715/744 |

(Continued)

FOREIGN PATENT DOCUMENTS

EP    1477880 A2 * 11/2004    ............. G06F 21/62

OTHER PUBLICATIONS

International Search Report and Written Opinion in International Application No. PCT/US2015/010203, mailed Apr. 15, 2015.

(Continued)

*Primary Examiner* — Bassam A Noaman
(74) *Attorney, Agent, or Firm* — Cognition IP, P.C.; Edward Steakley; Saleh Kaihani

(57) ABSTRACT

Disclosed are methods and systems for a computing environment that allows an operator to maximize or increase compliance with one or more data and privacy standards. In one embodiment, compliant and non-compliant sources are identified and exchange of data between those sources are blocked, partially allowed or allowed with regulation-compliant encryption of data.

22 Claims, 5 Drawing Sheets

(56) References Cited

U.S. PATENT DOCUMENTS

| | | |
|---|---|---|
| 2010/0251128 A1 | 9/2010 | Cordasco |
| 2011/0029963 A1 | 2/2011 | Smith et al. |
| 2011/0289140 A1 | 11/2011 | Pletter et al. |
| 2012/0102402 A1 | 4/2012 | Kwong |
| 2012/0204032 A1 | 8/2012 | Wilkins et al. |
| 2012/0216122 A1 | 8/2012 | Wong et al. |
| 2013/0215116 A1 | 8/2013 | Siddique et al. |
| 2014/0019892 A1 | 1/2014 | Mayerhofer |
| 2014/0157256 A1* | 6/2014 | Marshall ............... G06F 21/554 717/178 |
| 2015/0261956 A1* | 9/2015 | Anderson ............... G06F 21/57 726/22 |
| 2016/0232322 A1* | 8/2016 | Mensinger ............. G16H 50/30 |
| 2016/0269418 A1* | 9/2016 | Sangary ................. G06F 21/44 |
| 2016/0328576 A1 | 11/2016 | Howley |
| 2017/0315790 A1 | 11/2017 | Samatov et al. |
| 2018/0046765 A1* | 2/2018 | Notani ................... G16H 10/60 |

OTHER PUBLICATIONS

International Search Report in International Application No. PCT/US2018/053040, mailed Dec. 11, 2018.

* cited by examiner

FIG. 5

SYSTEMS AND METHODS FOR REGULATION COMPLIANT COMPUTING

CROSS-REFERENCE TO RELATED APPLICATIONS

This application is a 35 U.S.C. § 371 national stage application of PCT International Application No. PCT/US2018/053040, filed on Sep. 27, 2018, the contents of which are incorporated herein.

BACKGROUND

This invention relates generally to methods and systems for displaying, grouping and linking software applications in a manner to increase or maximize compliance with one or more data regulation regimes, and in particular an interactive display platform and system and methods of displaying, accessing and interacting with online applications and regulated content in a manner that maintains compliance with one or more data regulation standards.

DESCRIPTION OF THE RELATED ART

In today's technology, users have access to several different web browsers. While the web browsers operate more or less the same, each one offers some unique capabilities. However, some sectors require such high levels of security and protection of user data that the commercial browsers such as Chrome®, Internet Explorer®, Safari® or Firefox® cannot meet. Among these sectors are companies that handle individuals personally identifiable data.

Health care providers, for example, in many jurisdictions are required to abide by strict privacy and data regulation laws. For instance, in the United States, the Health Insurance Portability and Accountability Act (HIPAA) is a law designed to provide privacy standards to protect patients' medical records and other health information provided to health plans, doctors, hospitals and other healthcare providers. HIPAA sets data privacy and security provisions for safeguarding medical information, such as medical records and other identifiable health information. Specifically, HIPAA privacy rules set standards for electronic patient health information (ePHI) data protection. HIPAA requires that the ePHI only be handled by authorized users. Additionally, the ePHI should not be tampered or altered during the transmission and could be transmitted only after being encrypted. Typically, an ePHI document has an identifier, identifying an individual, and health records of that individual. Common identifiers can include, patient's name, address, date of birth, email, social security number and telephone number. Common patient health data or record can include past, present or future medical data, diagnosis or prognosis, mental health data, treatments received and in some cases health care related payments may be considered regulated and protected ePHI data.

Other jurisdictions also have introduced legislation or regulation aimed at protecting health information or other sensitive content. For example, in recent years the European Union has introduced General Data Protection Regulation (the "GDPR"). The GDPR includes privacy laws related to healthcare as well as rules regulating other type of personal data. Other countries also have data privacy and regulations that can expressly or implicitly extend into sensitive industries like healthcare, finance, and communication networks. Besides HIPAA and GDPR, examples of data regulations can include Japan's Act on the Protection of Personal Information, South Korea's Personal Information Protection Act ("PIPA"), Asia Pacific Economic Cooperation ("APEC") Privacy Framework, China's National Standard on Personal Information Protection and Australian Data Privacy Regulation.

However, specifically related to HIPAA in the United States, there is no controlling government or government-delegated authority setting standards, protocols, or accreditation as to whether compliance is achieved. HIPAA auditors perform security review, training and compliance implementation programs. But even the auditors do not have set standards.

Therefore, software providers, for example, electronic health records, billing systems, and laboratory information systems, each independently create systems in attempt to comply with regulations. However, most of these systems do not meet all of the requirements of HIPAA. Even more, as soon as any of these otherwise compliant systems are accessed from a commercial web browser, they can become non-HIPAA-complaint.

Most software applications that might be otherwise regulation-compliant become non-compliant or vulnerable as soon as they are operated in or displayed in a regular, commercial web browser, such as Chrome® or Safari®. Non-compliance can be because, among other reasons, conventional web browsers allow saving, downloading, printing or viewing of any secured content or source. Existing solutions sometimes only maintain the regulation-compliance of the software provider utilizing those solutions, while leaving the end user (e.g., a physician office subject to HIPAA) still vulnerable to intentional or accidental violation. Some web applications make it more difficult for users to perform functions, such as right click of a mouse to access compliance-compromising features such as "Save Page As", "Show Page Source" or "Print Page" by implementing a client-side script. For example, some JavaScript® web applications include code, that when executed in a user's web browser, disable undesirable features, such as "Save As" in the executed program, and the user can't accidentally or intentionally access them.

However, the user running such applications via a multi-tab web browser, can still access regulation-compromising features of the browser when interacting with other open tabs running potentially non-compliant programs. In other words, existing solutions cannot globally disable the regulation-compromising features of the browsers in which they are run. They can only control the user's compliance as it relates to their own program. Such solutions therefore work towards achieving compliance for the program developer, while the end user of the program can still be exposed to data regulation violation.

Additionally, such solutions are not commonly adopted because they are expensive, difficult to implement and maintain, and cannot be easily monitored or audited. Moreover, HIPAA compliance rules may prohibit even the temporary local storage of ePHI data in any readable format. Therefore, the "Save Page as . . . " feature of available web browsers is by definition a violation. In fact, users can save a web page with any ePHI data as easily as pressing "Ctrl+s" and that data becomes stored on a file on a local device and subject to further disclosure or distribution. This is still an issue even when the user is offline and no longer has reason to access that data. Additional browser features with the same compliance concerns include, but are not limited to, "Print", "Print to PDF", "View Source", "Make Available Offline" and all "Developer Tools". Because these are standard features in commercial web browsers, programs running in those browsers cannot disable those features, or remove them from the browser menus or stop the browsers from accessing the undesirable HTML content. Additionally, since browsers are designed for mass market appeal, there is limited incentive for browser companies to address these issues.

Moreover, substantial financial resources have to be expended on data regulation compliance efforts, while achieving compliance using existing technology remains uncertain. Private enterprise and many small businesses, for example, health care practices, find themselves unable to achieve good compliance rate using existing technology. Performing frequent compliance audits can also put an additional burden on small businesses while not increasing their compliance rate.

As described above, the Health care industry is not the only industry where protection of data and user privacy have gained global importance. Businesses of all sizes, even individuals, find themselves having to comply with government issued regulations on data security and privacy. As described above, the design and features of conventional computing environments, such as conventional web browsers make compliance in many cases impossible or inordinately expensive to achieve.

Therefore, there is a need for a regulation-compliant computing environment with features, that ensure or maximize compliance with various data regulatory regimes.

SUMMARY

In one aspect, various implementations disclosed herein enable a computing system to assess regulation compliance of a requested application, in which an application engine generates the requested application including a user interface. The system may include a user interface controller to modify the user interface, based on input from a compliance engine to disable or eliminate regulation compromising features of the requested application.

In some embodiments, the user interface controller generates a display Act including a display Pod, where the display Pod includes the modified user interface of the requested application. In some embodiments, the user interface controller generates multiple display Pods within an Act, wherein each display Pod is associated with a requested application.

In some embodiments, related fields between display Pods are linked, wherein linking includes secured exchange of content between related fields based on one or more data regulation standards. In some embodiments, an automatic or manual exchange of data between display Pods of compliant applications and display Pods of non-complaint applications are blocked or performed through secured connections or preformed while generating a visual warning.

In some embodiments, the compliance engine determines compliant and non-compliant requested applications and restricts exchange or transfer of regulated data to a non-compliant requested application.

In some embodiments, the modification of the user interface includes one or more of redaction of regulated content, disabling or eliminating menu options and program modules directed to data regulation compromising features.

In some embodiments, the computing system further includes a compliance database including tables, lists, keywords, and/or libraries based on which regulation compliance of the requested application is determined.

In some embodiments, the compliance database is updated by artificial intelligence techniques.

In another aspect, a computer-implemented method is disclosed, wherein the method includes receiving a user request to display an application; determining regulation compliance of the requested application; and modifying the requested application and a user interface of the requested application to disable or eliminate regulation compromising features of the requested application.

In one embodiment, the method further includes modifying the requested application and the user interface of the requested application to add data regulation compliance features. In another embodiment, the method further includes: receiving a second request from the user to access a second application; determining regulation compliance of the second application; and blocking exchange of content between the requested applications if the second application is non-compliant.

In one embodiment, receiving a user request to access an application further includes receiving the user request to access content; determining whether the content comprises regulated data; and protecting the regulated data from regulation compromising action of the user and the requested application.

In another embodiment, the method further includes: accessing or displaying two or more applications simultaneously; determining related fields of content between the accessed applications; linking the related fields with secured connections such that content can be exchanged between the linked, related fields through the secured connections.

In some embodiments, the method further includes establishing preconfigured user interface displays of applications, wherein related fields in the applications associated with the user interfaces are linked.

In another aspect, a computer-implemented method is disclosed, The method includes: receiving a user request to access one or more locally-stored content or web-based applications capable of viewing or editing the content; accessing the requested applications; establishing display Pods for accessed applications and requested content, wherein an accessed application is run with a user interface generated in a display Pod and establishing a display Pod comprises accessing a rendering engine of the requested application; linking related content fields between the accessed applications and the display Pods, wherein the linking enables a manual or an automatic exchange of content between accessed applications and files storing the related content; determining whether an accessed application is compliant with one or more data regulation standards intended to protect regulated data; and establishing secured connections between compliant applications and non-compliant applications, such that the automatic or manual exchange of content between the compliant applications and the non-compliant applications are performed through secured connections.

In some embodiments, the regulation standards include HIPAA regulations intended to protect electronic patient health information (ePHI) and determining compliance includes running a compliance audit script on accessed applications.

In one embodiment, the compliance audit script determines whether the accessed application performs transport encryption, backup, authorization, storage encryption, maintains ePHI data integrity, when commanded permanently disposes ePHI data and whether the accessed application is stored on HIPAA compliant servers.

In one embodiment, the accessed applications include web browsers, webpages or applications running on webpages, word processors, spreadsheets, accounting applications, online gaming applications, video or imaging applications, and/or PDF editors.

In some embodiments, the method further includes generating a visual and/or auditory alarm or warning when determining an accessed application is non-compliant.

In some embodiments, the method further includes searching for indicia of regulated data, scanning the accessed content, application and/or servers where the accessed applications reside for regulated data; and encrypting and/or redacting the regulated data automatically or via receiving a user command.

In some embodiments, the secured connections comprise enforcing SSL encrypted connections.

In some embodiments, the method further includes receiving a request to store data; determining whether the data comprises regulated data; encrypting the regulated data; and storing the regulated data and remaining data.

In some embodiments, the method further includes determining an attempt of the manual or automatic exchange of content comprising regulated data to a non-compliant accessed application; blocking the exchange; displaying an auditory and/or visual warning message; and cancelling the exchange or removing the regulated data and allowing the exchange.

In some embodiments, the method further includes determining an attempt to share regulated data based on receiving an input of a first user or based on receiving a request from a second user; determining an appropriate scope of the regulated data to be shared in part based on the received request of the second user, a profile, access level and credentials of the second user and/or a purpose of sharing regulated data; redacting or removing the regulated data outside the appropriate scope; and sharing the regulated data.

In another aspect, a non-transitory computer storage that stores executable program instructions is disclosed. When executed by one or more computing devices, the instructions configure the one or more computing devices to: receive a user request to access one or more locally-stored content or web-based applications; access the requested applications; establish display Pods for accessed applications and requested content, wherein an accessed application is run with a user interface generated in a display Pod and establishing a display Pod comprises accessing a rendering engine of the requested application; link related content fields between the accessed applications and the display Pods, wherein the link enables a manual or an automatic exchange of content between accessed applications and files storing the related content; determine whether an accessed application is compliant with one or more data regulation standards intended to protect regulated data; and establish secured connections between compliant applications and non-compliant applications, such that the automatic or manual exchange of content between the compliant applications and the non-compliant applications are performed through secured connections.

In one embodiment, the regulation rules include HIPAA regulations intended to protect electronic patient health information (ePHI) and determining compliance includes running a compliance audit script on accessed applications and never storing the exchanged data outside of the applications involved in the exchange.

In some embodiments, the compliance audit script determines whether the accessed application performs transport encryption, backup, authorization, storage encryption, maintains ePHI data integrity, when commanded permanently disposes ePHI data and whether the accessed application is stored on HIPAA compliant servers.

In another embodiment, the accessed applications comprise web browsers, webpages or applications running on webpages, word processors, spreadsheets, accounting applications, online gaming applications, video or imaging applications, and/or PDF editors.

In some embodiments, the non-transitory computer storage is further configured to generate a visual and/or auditory alarm or warning when determining an accessed application is non-compliant.

In another embodiment, the non-transitory computer storage is further configured to: search for indicia of regulated data; scan the accessed application and/or servers where the accessed applications reside for the regulated data; and encrypt and/or redact the regulated data automatically or via receiving a user command.

In one embodiment, the secured connections include enforcing SSL encrypted connections.

In another embodiment, the non-transitory computer storage is further configured to: receive a request to store data; determine whether the data comprises regulated data; encrypt the regulated data; and store the regulated data and remaining data.

In some embodiments, the non-transitory computer storage is further configured to: determine an attempt of the manual or automatic exchange of content comprising regulated data to a non-compliant accessed application; block the exchange; display an auditory and/or visual warning message; and cancel the exchange or remove the regulated data before allowing the exchange based at least partly on an input from the user.

In one embodiment, the non-transitory computer storage is further configured to: determine an attempt to share regulated data based on receiving an input of a first user or based on receiving a request from a second user; determine an appropriate scope of the regulated data to be shared in part based on the received request of the second user and/or a purpose of sharing regulated data; redact or remove the regulated data outside the appropriate scope; and share the regulated data.

In another aspect, a computer-implemented method is disclosed. The method includes: establishing a display comprising one or more Acts, wherein an Act comprises one or more Pod displays; receiving a request to access an application; generating a regulation-compliant version of the requested application based on a set of regulation standards; receiving a request for content to be accessed by the requested application; establishing a Pod display for regulation-compliant application; and allowing the regulation-compliant application to access the content.

BRIEF DESCRIPTION OF THE DRAWINGS

These drawings and the associated description herein are provided to illustrate specific embodiments of the invention and are not intended to be limiting.

FIGS. 3-5 illustrate examples of interactive displays which can be generated by the system of FIG. 1.

DETAILED DESCRIPTION

Figure 1:
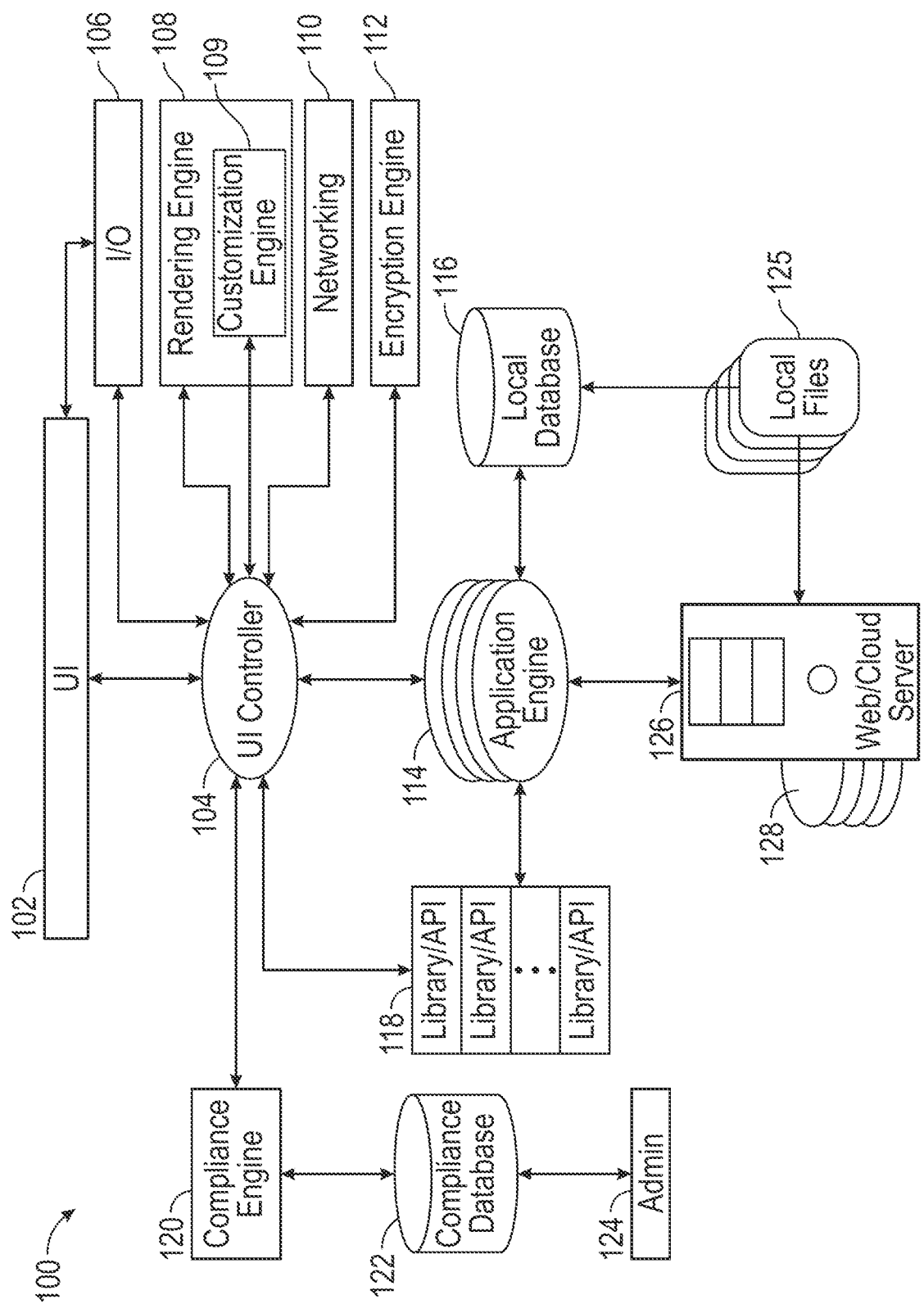
FIG. 1 illustrates a system for producing a computing environment to ensure or increase compliance with one or more data regulation standards.

The following detailed description of certain embodiments presents various descriptions of specific embodiments of the invention. However, the invention can be embodied in a multitude of different ways as defined and covered by the claims. In this description, reference is made to the drawings where like reference numerals may indicate identical or functionally similar elements.

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

Definitions

When the terms "one", "a" or "an" are used in the disclosure, they mean "at least one" or "one or more", unless otherwise indicated.

Communication interfaces can communicate data using one or more wireless communication protocols such as Bluetooth, Bluetooth Low Energy (BLE), ZigBee, Wi-Fi, 802.11 protocols, Infrared (IR), Radio Frequency (RF), 2G, 3G, 4G, etc., and/or wired protocols and media. In some aspects and/or in some parts a communication interface can communicate via a communication platform, which may include one or a combination of the following: an Internet connection, such as a local area network (LAN), a wide area network (WAN), a fiber optic network, internet over power lines, a hard-wired connection (e.g., a bus), and the like, or any other kind of network connection. Communication platform may be implemented using any combination of routers, cables, modems, switches, fiber optics, wires, radio (e.g., microwave/RF links), and the like. Further, communication platform may be implemented using various wireless standards, such as Bluetooth®, BLE, Wi-Fi, 3GPP standards (e.g., 2G GSM/GPRS/EDGE, 3G UMTS/CDMA2000, or 4G LTE/LTE-U), etc. Upon reading the present disclosure, one of skill in the art will recognize other ways to implement communication platform for facilitating communications between the various parts of the described system, Japan's Act on the Protection of Personal Information, South Korea's Personal Information Protection Act ("PIPA"), Asia Pacific Economic Cooperation ("APEC") Privacy Framework, China's National Standard on Personal Information Protection and Australian Data Privacy Regulation.

The term "processor" can refer to various microprocessors, controllers, and/or hardware and software optimized for loading and executing software programming instructions or processors including graphical processing units (GPUs) optimized for handling high volume matrix data related to image processing.

The term "regulated data" can refer to data in digital form that may be subject to one or more regulatory regimes in one or more jurisdictions. Examples of regulatory regimes and/or standards include, HIPAA, GDPR, Japan's Act on the Protection of Personal Information, South Korea's Personal Information Protection Act ("PIPA"), Asia Pacific Economic Cooperation ("APEC") Privacy Framework, China's National Standard on Personal Information Protection and Australian Data Privacy Regulation.

Data regulation and privacy concerns have recently gained importance and prominence on a global scale. For example, the European Union (the EU) has in recent years strengthened and heightened its regulation on data by implementing the General Data Protection Regulation ("GDPR"), which places a higher burden on companies and even individuals to ensure data protection and privacy. Additionally, governments and regulators place a higher burden on some industries, for example health and financial industries, to protect their user's data and privacy.

Meanwhile, businesses handling regulated data are left with tools that are less than adequate for ensuring compliance on their day to day business activities. For example, many physician offices and pharmacies handle HIPAA protected data. Various vendors and software developers provide software programs to these businesses. Available programs can range from programs that help health professionals in disease diagnose and treatment, medication prescription and software directed to administration of a health or medical practice. Examples of software used can include medical imaging software, laboratory software, billing, record keeping, accounting, and similar programs. In addition, any business may have to collect and process personally identifiable information on individuals where such data may be subject to GDPR or other data privacy regulations and regimes depending on the applicable jurisdiction.

Many software programs used by businesses subject to data regulation are web applications or software that run in a cloud environment. Businesses commonly use a commercially available web browser, for example, Internet Explorer®, Safari®, Chrome®, or Mozilla Firefox® to run web applications needed to conduct their business activities. However, commercial and general-purpose web browsers have been focused on general purpose and open, accessible, ready-to-order interoperability and were not designed for users that may require reliable and secure handling of regulated data with strict access management and security restrictions. Consequently, many businesses find themselves inadvertently violating their legal obligations on handling protected and regulated data. For example, commercial web browsers allow, copy/paste, save-as, print, view, share, email and other operations that can violet the legal obligations of a custodian of regulated data.

Some businesses attempt to increase compliance by establishing processes and procedures via employee conduct policy. However, such processes, procedures and policies remain vulnerable to human error or malice. Consequently, a computing environment designed with data regulation compliance features can help custodians of regulated data achieve a higher degree of compliance.

FIG. 1 illustrates a system 100 for a computing environment to ensure or increase compliance with one or more data regulation standards or regimes. The system 100 can run locally as a desktop or mobile application on a desktop or mobile computing device having a processor, memory, storage and input/output (I/O) devices. In some embodiments, the system 100 can run as a web browser. The system 100 can generate a regulation compliant User Interface (UI) 102 and the user can interact with the system 100 via the UI 102.

The UI 102 can be an interactive display platform used to generate one or more multi-view display scenes (Acts). An Act, in turn, can contain one or more primary content display blocks (Pods). Each Pod may be an interactive, customizable individual program segment that can display any file type, website, web application, application programming interface (API), document, social network activity or blog post, or any other interface. The interactive display platform of UI 102 may include more than one active session. The details of the UI 102 will further be described in relation to the embodiments of FIGS. 3-5.

The UI 102 can be controlled, and/or in some embodiments, be generated by a UI controller 104 to ensure compliance or to reduce the likelihood of a data regulation violation. The UI controller 104 can include or interface with an I/O module 106, a rendering engine 108, a networking module 110 and/or an encryption engine 112.

The UI controller 104 can receive user's interactions, inputs and commands via the I/O module 106 and update the display of UI 102. The I/O module 106 includes the communication protocols and rules for interacting with the display of UI 102. The UI controller 104 can utilize a rendering engine 108 to update the views of the display of the UI 102 based on user interactions received from the I/O 106. The networking module 110 can provide internet and/or cloud access to one or more parts of the system 100 and/or remote or web-based resources to update the UI 102. An encryption engine 112 can be configured to handle encryption services within and/or without system 100 to ensure compliance with data regulations. The encryption engine 112 can utilize technologies such as SSL encryption, public/private key, symmetric encryption algorithms such as Advanced Encryption Standards (AES) 128-bit encryption (key lengths of 128, 192 and 256 bits) and/or other encryption technologies available to web applications and databases.

While the UI controller 104 in FIG. 1 is shown as a single component, it can be implemented in multiple modules or be comprised of multiple modules which implement the functionality of the UI controller 104.

The UI controller 104 can interface with one or more Application Engines 114 depending on user interactions received from the UI 102. The UI controller 104 has access to one or more program libraries and/or Application Programming Interfaces (APIs) 118 and can load local content or web-based applications to update the display of UI 102. The UI controller 104 can load web-based applications and local content in a manner that the display and interfaces available to the end user are data regulation compliant. For example, when a user commands accessing a PDF file containing regulated data, the UI controller 104 can load a PDF reader interface with compliance-compromising features absent or disabled.

Notably, the UI controller 104 may only partially load a user requested application and/or content to ensure compliance with data regulations. In other embodiments, the UI controller 104 can build and load a user requested application using Application Engines 114 and library/APIs 118 but modify the user interface subroutines and/or libraries of the requested application to present a UI 102 that is regulation compliant. The UI controller 104 can interface with multiple Application Engines 114, depending on the content or applications requested by the user of system 100.

The UI controller 104 is able to modify or replace the content and/or user interfaces of applications associated with a user request to comply with data regulations. For example, when a user commands and/or requests opening a web application Uniform Resource Locator (URL), the UI controller 104 can load libraries and an Application Engine 114 directed to providing web browsing functionality, but the libraries 118 and/or Application Engine 114 can be dynamically modified and/or be previously modified to generate a custom web browser application lacking the data compromising features such as save-as, print, firebug module, view-source and others. The Application Engine 114 can interface locally, or via internet or cloud with one or more content sources such as local database 116 containing local files 125 and/or a web/cloud server 126 where regulated and/or unregulated content may reside in order to service the functioning of the underlying application called by the UI controller 104.

In some embodiments, the UI controller 104 modification of the Application Engine 114 and/or library/APIs 118 can include adding user interface features, subroutines, libraries and data flow, which can assist a custodian of regulated data in achieving a higher compliance rate. For example, the UI controller 104 can generate and/or modify the UI 102 to include menu options for highlighting regulated data, redacting regulated data and/or securing or restricting exchange of regulated data between compliant and non-compliant applications.

Unlike conventional web applications, which might be applications built to operate on top of a database, the UI controller 104 can be implemented as an application to operate on top of other web applications. In this embodiment, the UI controller 104 need not recreate the client-side, server-side or network-side processes associated with an Application Engine 114 and/or the library/APIs 118, such as cookies, security, firewall, networking, rendering, caching, or other functionality. Instead, the UI controller 104, alone or in combination with other components described herein, can modify the processes of the underlying web-applications to achieve data regulation compliance. For example, in one embodiment, the UI controller 104 can load and execute a web application (e.g., a web-based word processor) from the web/cloud server 126 but discard and/or modify the application's user interface and present a regulation-compliant user interface instead, while maintaining all other regulation-compliant software processes unaltered.

In some embodiments, the Application Engine 114 and/or library/APIs 118 may be a web application and reside in the cloud or be part of the web/cloud server 126 with its own server-side database 128. Examples include web-based word processor, spreadsheet or any other web-based applications such as Google® Docs or Google® Sheets. The UI controller 104 can allow most or all compliant processes of such applications to directly pass through to the UI 102.

Additionally, a compliance engine 120 can provide services to the UI controller 104 directed to ensuring and/or maximizing compliance. For example, the compliance engine 120 can run compliance audit scripts on accessed applications or resources, scan content for regulated data, flag regulated data, tag regulated data based on authentication credentials, tag regulated data for transport or storage encryption, generate alarms and warnings, automatically generate and save audit trails and/or reports, execute backup scripts based on classification of regulated data, permanently dispose of regulated data, tag regulated data for redaction and other functions based on the data and its regulatory regime.

The compliance engine 120 can interface with a compliance database 122 to provide data compliance related services. For example, the compliance database 122 can include tables, lists, library of rules, authentication databases and/or storage databases to facilitate the services of the compliance engine 120.

In some embodiments, an administrator of the system 100 can utilize the computing resources ADMIN 124 to modify or update the compliance database 122, for example, by adding/updating library of rules or keywords, etc. to ensure compliance. In other embodiments, artificial intelligence (AI) alone and/or in combination with human operators can improve compliance rate by running automatic tests, audits and other scripts to fine-tune or improve tables, rule libraries, databases and variables within the compliance database 122 for future use. For example, when the system 100 is implemented in an appropriate scale, AI techniques including statistical techniques, machine learning, deep learning, artificial neural networks and other AI technology can be used to improve the functionality of the compliance database 122 and associated components, for example by improving the rate of detecting and flagging non-compliant applications and/or features, reducing detection errors, fine-tuning variables or variable weights used to determine compliance.

Additionally, aspects of security and/or encryption within the system 100, in some embodiments, can be implemented using blockchain technology including public blockchains, private blockchains and/or consortium blockchains. For example, aspects of blockchain technology can be used to keep a trusted ledger and/or audit trail of transactions that may be subject to data regulation.

The user of the UI 102 may be a human operator and in some cases, may not be aware of or willing to follow employer-designated data compliance policies and procedures. In some cases, employees can accidentally compromise employer's compliance. For example, the user may be one of personnel in a physician's office. In the course of performing his job duties, or for personal reasons, the user may request opening websites or applications that may not be regulation compliant, while the user is also handling regulated data. The compliance engine 120 can monitor commands, requests and/or inputs received at the UI controller 104, consult its compliance database 122 and cause the UI controller 104 to take appropriate action. For example, compliance engine 120 may recognize and tag a web application as non-compliant. The UI controller 104 can limit transmission of data from other applications to the tagged non-compliant application.

Figure 2:
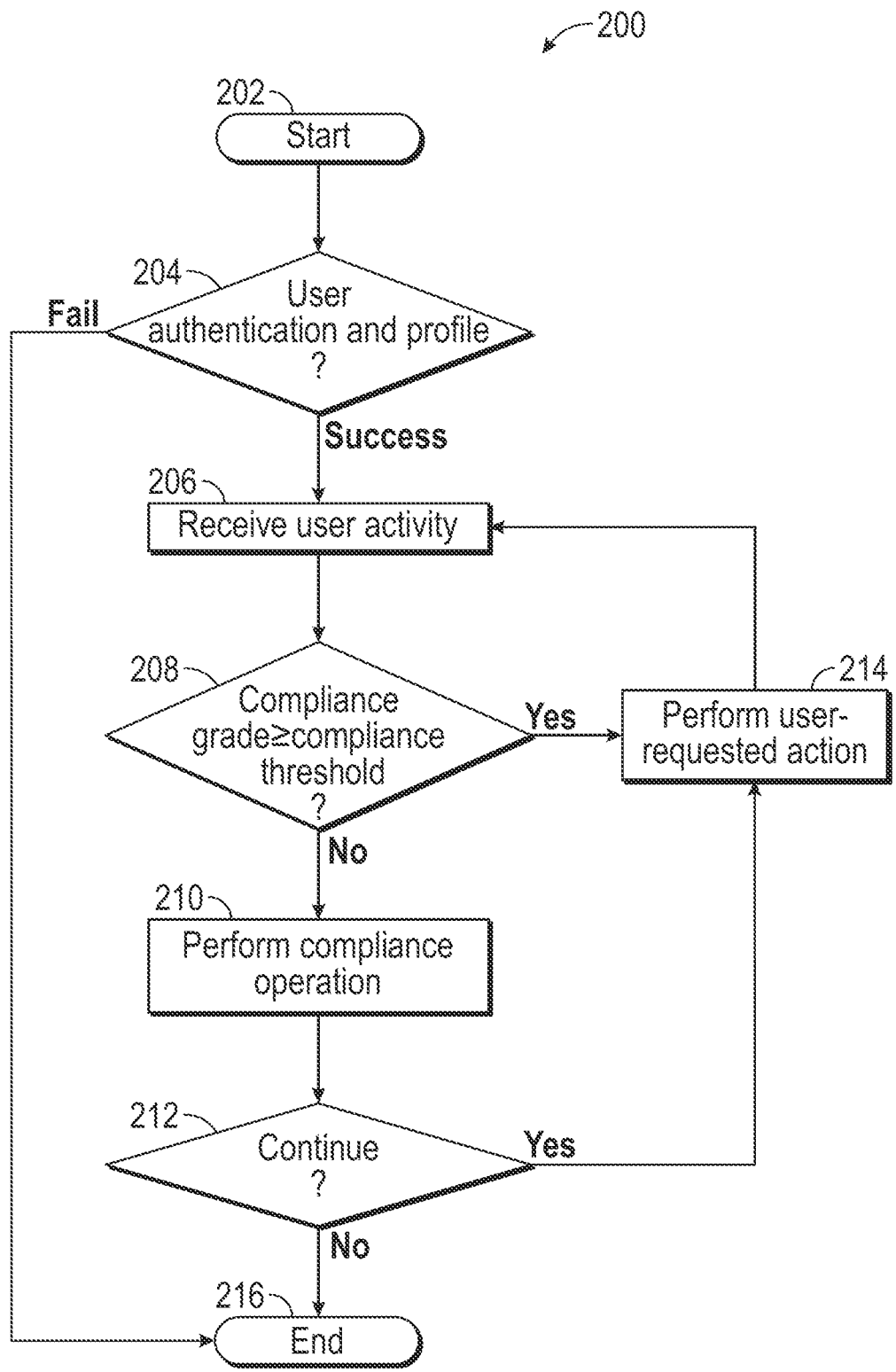
FIG. 2 illustrates a flow chart of an example operation of the system of FIG. 1.

FIG. 2 illustrates a flow chart 200 of an exemplary operation of the system 100. The process starts at the step 202. At step 204, the UI controller 104 performs user identification, authentication and loading of any relevant user profile, settings and configurations. The rendering engine 108 generates and displays a UI 102. In some embodiments, the rendering engine 108 can further include a customization engine 109, which can render the display of UI 102 based on user's personal settings, credentials or other associated user profile data. Such profile data can be stored in the local database 116. The compliance engine 120 can monitor/query the user's credentials to determine the appropriate level of access and treatment of regulated data. If user authentication at step 204 fails, the process ends at the step 216 and the user's access to the system 100 can be denied.

If the user authentication and/or loading of user profile data at step 204 succeeds, the process continues to the step 206, where the UI controller 104 can receive a user activity via the UI 102. For example, the user, via an input device such as a keyboard, keypad, mouse, touchpad display or similar devices can request to open or access an application as a Pod within an Act to be generated in the UI 102. The process then moves to the step 208, where the compliance engine 120 can assess a compliance grade for a user-requested application/content. If the compliance grade is at or above a predetermined compliance threshold, the process can continue to the step 214 where the user requested action (e.g., loading of application/content) can be performed. The process then continues at the step 206 receiving additional inputs from the user. If the compliance grade is below the predetermined compliance threshold, the process 200 can go to the step 210 and perform a compliance-related action.

Compliance-related operations can include the compliance engine 120 auditing the requested application/content and taking an appropriate action via the UI controller 104. For example, depending on the nature of the user action/command, the compliance engine 120 can allow the action, block the action, partially allow the action (e.g., allow data transmission with appropriate redactions), allow the action but generate alerts/warnings and/or perform parallel or background compliance and/or maintenance procedures. For example, the UI controller 104 can allow access and load a non-compliant web application in a Pod, but generate the UI 102 such that a prominent red-border is displayed around the non-compliant Pod clearly alerting the user.

The process then moves to the step 212 where depending on the action performed in the step 210 the process may terminate at the step 216 or may continue to the step 214. For example, if the user-requested action is allowed or is partially-allowed, the process moves to the step 214 and further continued to the step 206 by receiving more user commands/activities. If the user-requested action is blocked, the process ends at the step 216.

Compliance Grade and Minimum Compliance Threshold

The compliance engine 120 can determine a compliance grade for a user requested application/content by for example, checking for a set of predetermined criteria and assigning numerical values and weights. The criteria for a requested web application can include whether the application can and/or does perform regulation required activity, such as backup, encryption, authentication and/or whether the web application is from a trusted source and/or previously audited internal server.

Depending on the data regulation standard, a minimum compliance threshold can be defined. Applications or content whose compliance grade are determined to be below the minimum compliance threshold can be blocked or subject to further processing by the compliance engine 120. As described, the minimum compliance threshold can depend on the regulation standards and contexts in which the system 100 is implemented.

Context Aware User Interface to Increase Data Regulation Compliance

In some embodiments, the UI controller 104 can be context-aware, and depending on the context of data regulation and user activity, can perform one or more actions visible to the user and/or as background operations to aid in achieving a higher regulation compliance rate. In some embodiments, the UI controller 104 can allow the user to preconfigure, define and/or customize a computing environment in which regulated data can be handled with increased compliance. These actions can include grouping a set of web applications needed to perform one or more interrelated job functions, where the context of the jobs is handling regulated data; preconfiguring Acts to open interrelated applications in Pods within an Act, where the Pods are directed to the performance of one or more interrelated job functions; field-linking and automatic or user-aided intelligent field population and/or form filling among other context-related user interface operations.

For ease of description and as an example, the user of the UI 102 might be a member of staff in a medical office and may request accessing an electronic medical record (EMR) application (e.g., an EMR as a web application) in a Pod within an Act. The UI controller 104 can load a custom application directed to and/or based on the context of the Act in which the user-commanded application is to be run and the present configuration of the UI 102. For example, the UI controller 104 can load an EMR web application into a general-purpose web browser Pod. The web browser Pod and its associated user interfaces, as generated by the UI controller 104 and displayed in the UI 102, can be dynamically or previously modified to be regulation compliant.

As another example, the UI Controller 104 can automatically load complementary web applications as Pods when the user requests accessing a relevant web application. The UI controller 104 can additionally pre-populate fields based on content available in relevant Pods and perform background regulation compliance procedures to make the user experience less error prone and increase regulation compliance. For example, a profile and user history of a member of staff in a physician office might indicate that the user routinely accesses an EMR web application followed by accessing a Lab Order Requisition (LOR) form (e.g., in a PDF editor Pod). The user then transfers potentially regulated data and content (e.g., a patient's name, date of birth, and address) from the EMR web application to the LOR Pod. The UI controller 104 can be context-aware. When the user requests loading the EMR web application into a Pod, the UI controller 104, in addition to loading the requested EMR web application, can automatically load a LOR Pod, securely link the relevant fields between the EMR and LOR and pre-populate content from the EMR Pod to LOR Pod. Consequently, the user is freed from having to copy/paste regulated data from one application to another where regulation compliance can be compromised.

In other embodiments, the user can preconfigure, an Act and one or more Pods within the Act to open and link applications directed to interrelated job functions. Examples of linking can include operations such as detecting related, similar and/or identical fields between one or more active Pods (and/or their associated open applications), generating a secured connection between the linked fields, exchanging content between linked fields, automatically or semi-automatically via a user's review and confirmation.

Artificial intelligence techniques can be used to learn user behavior and improve the context detection and automatic intervention by the UI controller 104. When the system 100 is employed amongst a number of organizations, institutions or businesses handling regulated data, artificial intelligence techniques can be deployed to build rules databases, optimize variables and better predict situations where regulation-compromising computing takes place. Such knowledge-base can enable automatic intervention by the UI controller 104 to improve regulation compliance.

Simultaneous Active Pods

Most conventional interactive displays, for example a commercial browser having multiple tabs, only maintain one tab and its associated software process active at a time. While transitioning between tabs in such a browser may be seamless to the user; in fact, the conventional multi-tab browser stops functionality and processes of one tab when switching to another tab. For example, if a user cuts and pastes text from a first program in a first tab to a second program in a second tab, behind the scene and perhaps seamless to the user, the text is copied first into a clipboard and then pasted into the second program in the second tab. Every time the user transitions between tabs, operations of inactive tabs are halted and only the processes of the active tab are operational. In conventional browsers, the user may be forced to open a second instance of the browser in order to keep two tabs active at the same time.

Copy/pasting regulated data into a clipboard in some instances can be a violation of data regulations (e.g., a HIPAA violation). For example, any ePHI data copied that way will remains in Clipboard even when a copy/paste process is completed, there is no way to purge the Clipboard content without some special software, users can only replace it. Additionally, when the user opens different instances of the conventional multi-tab display, ensuring compliance becomes more challenging because multiple windows overlap and the processes in the multiple instances of the multi-tab displays are not connected in a way that data transfer between the processes can be monitored, checked, audited or manipulated by the conventional multi-tab-single-content-display technology.

Unlike conventional multi-tab displays, the described interactive display can contain Pods in an Act which can be active and connected simultaneously and the processes of each Pod can be monitored and audited by the UI controller 104. For example, two or more Pods can be active and connected in a display Act. A PDF viewer can be active in Pod 1 and a web-based billing application can be active in Pod 2. If the user inputs a command to copy text from the PDF viewer to the billing application, the UI controller 104 and the compliance engine 120 can detect if the text to be copied is regulated data. Depending on the implementation, the UI controller 104 can utilize a clipboard, but encrypt/decrypt the text before/after performing clipboard functions or can bypass clipboard function altogether. Because Pods 1 and 2 are active and connected simultaneously, the UI controller 104 can directly inject text from a field in Pod 1 to a field in Pod 2, without an intermediary clipboard. Other data compliance operations of the system 100 can also be facilitated or made possible by Pods in a display Act being able to be simultaneously active and connected.

The UI controller 104, the I/O module 106 and the rendering engine 108 can control inputs, outputs, displays and data transfers between the processes in Pods within the UI 102, thereby enabling a more comprehensive and accurate implementation of data regulation. For example, if the compliance engine 120 determines that the transfer of data from one Pod to another is an authorized sharing that compromises compliance, the UI controller 104 can block the transfer and generate an audible and/or visual warning to the user.

Building Custom-Regulation Compliant Applications

Additionally, the UI controller 104 has access to various programs, software, subroutines, and/or library/APIs 118, which enable the UI controller 104 to build custom, regulation-compliant applications from the existing libraries of general-purpose applications and present a data compliant version of those applications to the user of the UI 102. In some embodiments, the UI controller 104 can detect the content accessed by the operator of the UI 102 and depending on the content and the context, build the appropriate and regulation-compliant interfaces and I/O rules. For example, when the user of the UI 102 attempts to open a PDF file, the UI controller 104 can load the libraries and subroutines of a general-purpose PDF viewer from libraries 118, modify, disable or skip the regulation compromising features or libraries and render a custom, regulation-compliant PDF viewer where the menus and I/O rules are defined by the UI controller 104 based on input from compliance engine 120. The rendering engine 108 can render and present the custom, compliant PDF viewer and the associated compliant menu on the UI 102.

Examples of UI 102

Figure 3:
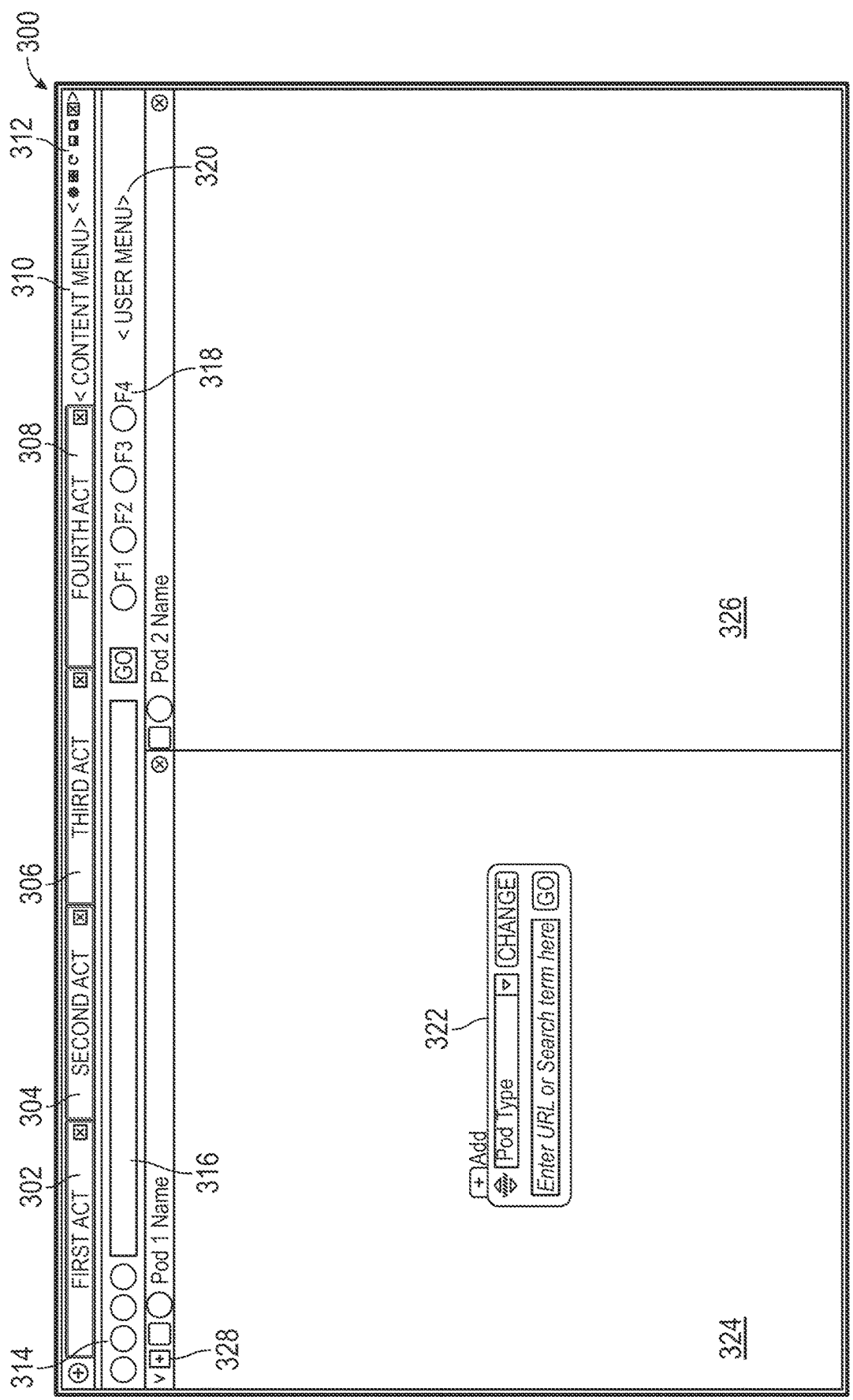

FIG. 3 illustrates an example interactive display 300 which can be generated by the embodiment of FIG. 1 as the UI 102. The interactive display 300 includes Acts 302, 304, 306 and 308. Each Act can include none, one, or multiple Pods. If an Act includes two or more Pods, the Pods can be simultaneously active and connected. In the example shown, Act 302 includes a first Pod 324 and a second Pod 326.

Content menu 310 and buttons 312 can relate to and implement the operations, functionality and settings of an active Act and/or the interactive display 300 as a whole. These functions and menus can include a setting menu, a refresh button, a customize view button, close all function or similar global and/or Act-specific command buttons. In some embodiments, user is able to customize the view, button functionality or other display features. Such user personalization can be saved in a user profile on the local database 116. Compliance engine 120 can monitor and audit the user customizations and settings and allow, block or partially allow user customizations based on input from the compliance database 122. A visual or textual warning may be generated via the UI controller 104 to inform the user of the action.

The buttons 314 can be generated with command buttons related to the current Pod. For example, if the current Pod is a web browser Pod, the buttons 314 can include common features such as forward, back, close window or refresh buttons. The UI controller 104 can dynamically change the menu 314 depending on which Pod the user is operating. In the case of web browser Pod, an address bar 316 can be displayed. Notably, while the processes of all Pods in an Act may be simultaneously active, the user may be interacting within one Pod at a time and the associated Pod menus can be updated accordingly.

Buttons 328 can be used to add Pods. The buttons 318 and menu 320 can be customized, contextually generated and displayed based on the context of the display 300 or the Acts 302-308. For example, a button F4 in buttons 318 can be a toggle switch that when turned on, automatically detects and tags regulated data in the displayed Pods. Further menu options can then be utilized to perform further actions while maintaining compliance. For example, regulated data may be partially shared when portions of the regulated data are redacted depending on the profile of the recipient of the data. In other embodiments, regulated data may be redacted in whole or in part for printing, viewing or presentation purposes. Another button F3 can be customized to display the shape of a shield, which the user may click to secure all transactions between regulation-compliant and non-compliant websites.

In some embodiments, a hovering menu 322 can appear automatically or based on a user input (e.g., a right click) when the user wants to open a new Pod. The hovering menu 322 allows the user to efficiently add or edit Pod settings, for example, by using a drop-down menu to choose the type of Pod the user desires to open.

Figure 4:
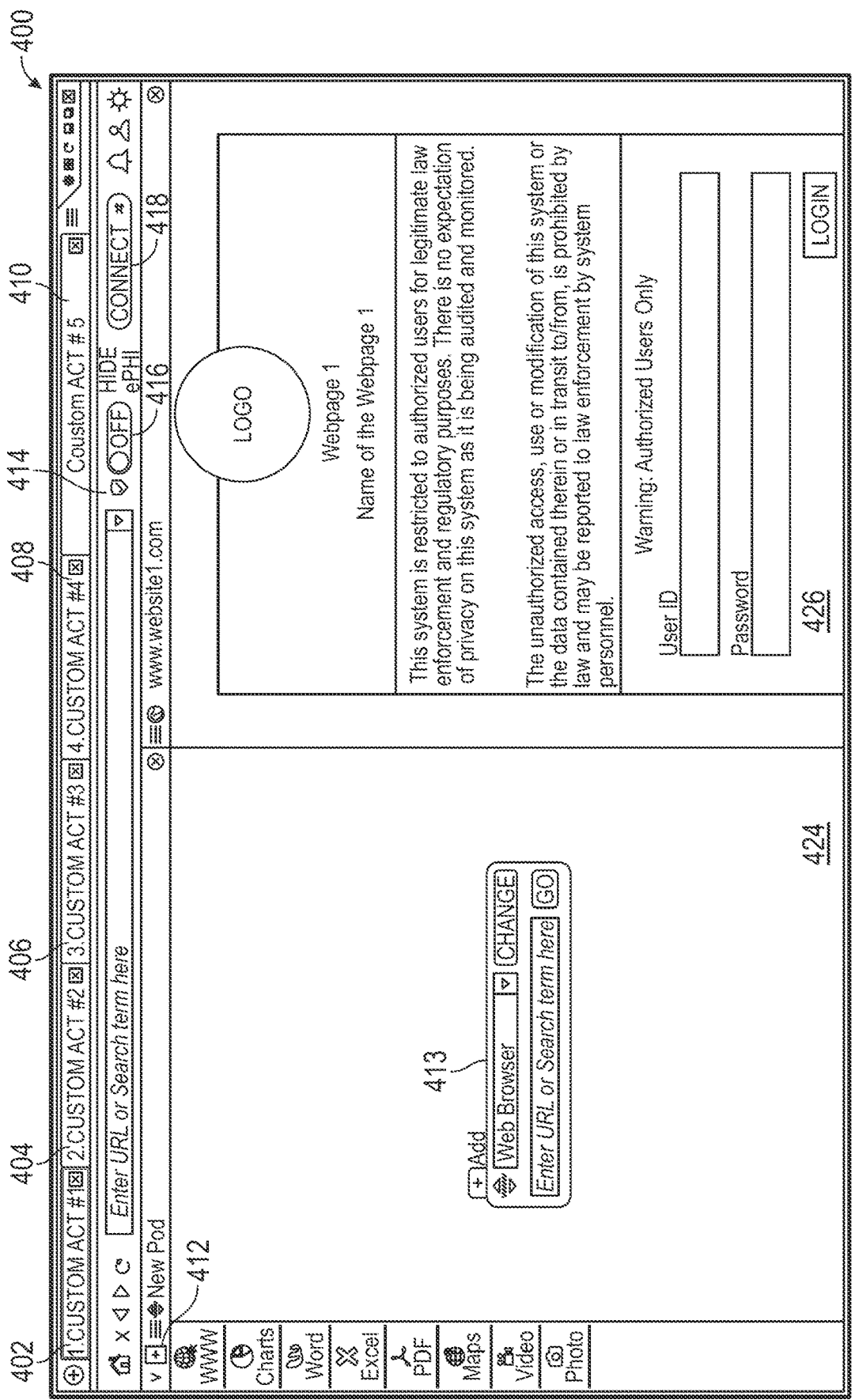

FIG. 4 illustrates an example interactive Presentation display 400 which can be generated by the embodiment of FIG. 1 as the UI 102. The interactive display 400 includes Acts 402, 404, 406, 408 and 410. As shown Act 402 is active and contains Pods 424 and 426. The user can choose the type of Pod the user wants to open in Pod 424 via buttons 412 or via hovering menu 413. Some example Pod options that the user might choose to open are web browser, graphing/reporting, word processing, spreadsheet, PDF, map or navigation, multimedia such as videos or photo Pods. Pod 426 is the current Pod and is a web browser Pod.

Buttons 414, 416 and 418 are built and displayed by the UI controller 104 based on the context of the Act 402 and its Pods 424 and 426. For example, button 414 can be rendered in the form of a shield. When the user clicks the button 414, the compliance engine 120 scans the open Pods and determines regulation-compliant Pods and non-compliant Pods. Transactions and interactions between compliant and non-compliant Pods can be performed using appropriate encryption. For example, in some embodiments, the UI controller 104 would secure the exchange of any regulated data by providing SSL Security.

Button 416 as described earlier can be customized to be a toggle on/off switch where upon turning on, regulated data (e.g., ePHI) is detected, tagged, redacted or subsequently treated securely by the UI controller 104. Button 418 can be customized and generated to be a "Connect" button. In some cases, an employee of a custodian of regulated data may have to transfer regulated data between various fields within two or more Pods, for example to fill a form using the exchange of data from one Pod to another. By pressing the Connect button 418, the operator can securely connect two or more Pods where similar or related fields are manually or automatically detected. The Operator can then exchange data between connected Pods by manual drag and drop or by confirming an automatic filling of a target form. Notably, in the background, the UI controller 104 and the compliance engine 102 monitor, audit and take appropriate measures to ensure connection or exchange of data does not compromise compliance.

The compliance buttons and menus described above are meant as examples. Additional and/or substitute menus and buttons depending on the type of regulation and the context of data can be generated and used. Alternatively, some or most of the compliance measures taken by the UI controller 104 and compliance engine 120 may be automatic and not apparent to the user. In other embodiments, and perhaps depending the operator credentials, the UI controller 104 can generate visual or textual alerts to inform the operator of actions taken or recommended to maintain compliance. For example, a red border or other visual alert can be displayed around or about a non-compliant website to alert the user that a website Pod is a non-compliant website. Additionally, the attempt to exchange data with the non-compliant web site can be blocked or only partially allowed with alerts and alarms informing the operator of the reasons for rejection or partial allowance.

As described, in some instances the custodian of regulated data or its employees may have to transfer data between regulation-compliant and non-regulation-compliant websites and/or web-based applications. The compliance engine 120 can distinguish between the compliant and non-compliant sources and take appropriate compliance measures. In some embodiments, the compliance engine 120 can run a compliance audit script on one or more active Pods. For example, in the context of HIPAA regulation, a website is HIPAA compliant if the website performs transport encryption, storage encryption, backup, authorization, and it is able to maintain data integrity and perform permanent disposal of ePHI data. Furthermore, accessing an external website in some instances is only HIPAA compliant if there is a HIPAA Business Associate Agreement on file and/or the accessed websites are not external and are hosted in-house and are properly secured per HIPAA rules.

The compliance audit script can check for the parameters above using a variety of techniques and assign a compliance grade to an accessed application/website. Alternatively, the compliance audit script can tag the accessed source as HIPAA compliant or as non-compliant. For example, the compliance engine 120 can perform tests on a target website by sending test packets, sending queries, checking its available source codes, looking for keywords or programming modules needed to achieve compliance in the areas above. In another embodiment, the compliance database 122 can maintain tables and databases of HIPAA compliant sources and/or keywords to check for, queries or tests to run or other tools that may identify a source's compliance.

Additionally, the compliance engine 120 is capable of identifying regulated data within the interactive display platform generated by system 100. For example, the compliance engine 120 can monitor the accessed data by monitoring the operations of the I/O module 106 and tag regulated data. Some regulated data can be data that includes a person's name, date of birth or other sensitive personal information such as social security number. The compliance engine 120 can tag the regulated data and later control its treatment. In another embodiment, the compliance engine 120, automatically or upon receiving a user input, can scan the open Pods in a Presentation display to identify and tag regulated data.

Figure 5:
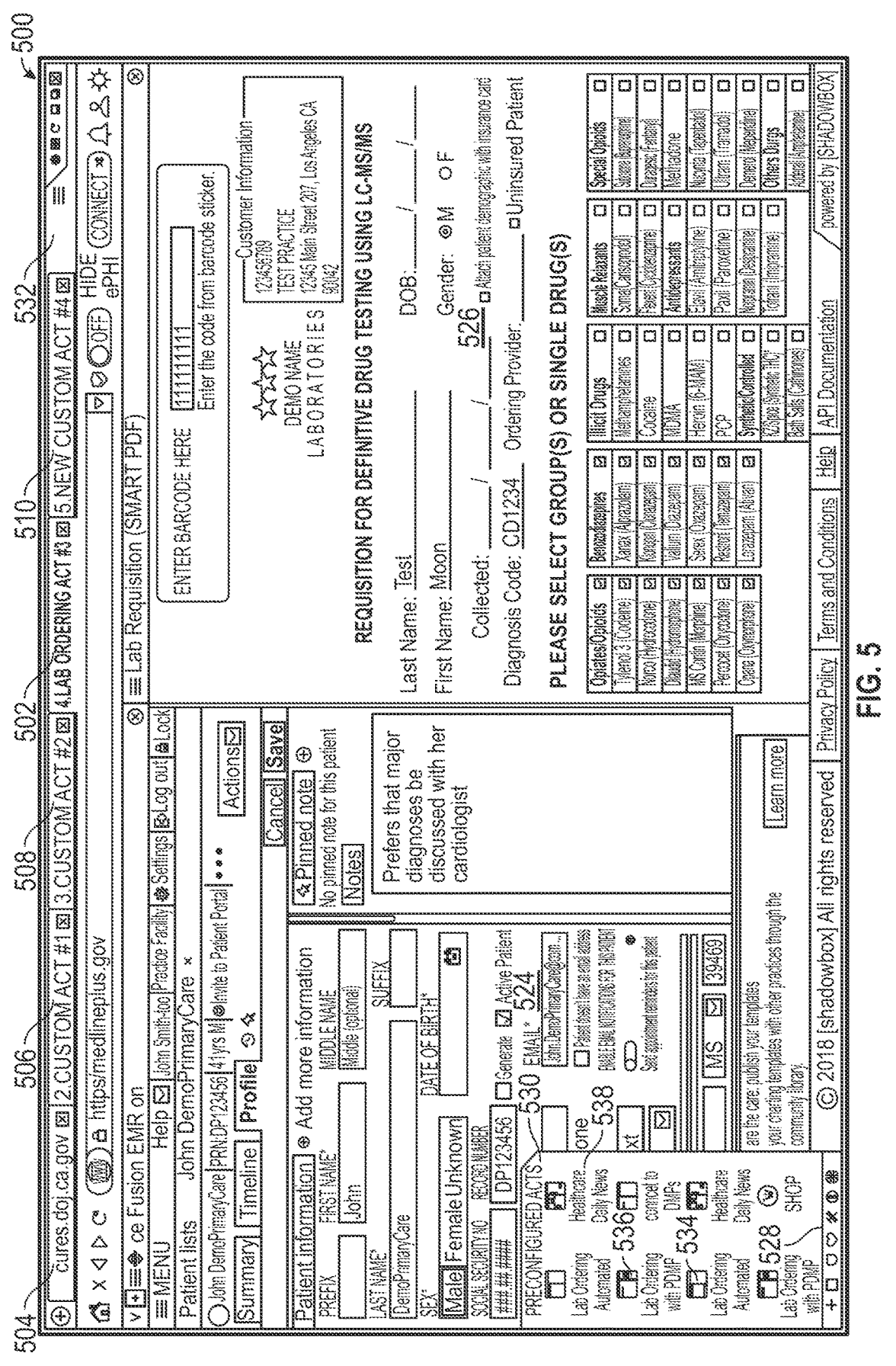

FIG. 5 illustrates an interactive display 500, which can be generated by the embodiment of FIG. 1 as the UI 102. The user of the interactive display 500 and/or admin personnel operating ADMIN 124 can create, customize, save and open pre-set or pre-configured Acts as the UI 102. Organizations handling regulated data can often increase their compliance rate if users are able to efficiently open and access their desired applications without clutter and distraction. Connected Pods with intelligent mapping of relevant/similar data fields according to the present embodiments can be used to minimize compliance compromising user actions, such as copy/pasting of data from one application to another. Automated or semi-automated similar field data mapping and field-population can be employed to increase compliance.

Preset or preconfigured display Acts are custom Acts that have been preconfigured with one or more display Pods directed to performance of one or more job functions that handle regulated data. For example, in the context of a health care provider office concerned with HIPAA compliance, a custom Act may contain application Pods directed to EMR and a laboratory report ordering application. Other examples of preconfigured Acts can include programs such as Prescription Drug Monitoring Program (PDMP) or Prescription Monitoring Program (PMP), reporting and business analytics programs (e.g., business intelligence software, such as Power BI®, Tableau®, Demo®, etc.). The preconfigured display Acts in turn can include one or more Pods directed at performing their respective functions.

The interactive display 500 includes pre-set Act 502 and custom acts 504, 506, 508 and 510. As shown Act 502 is active and contains pre-set EMR Pod 524 and a Lab Ordering Requisition (LOR) Pod 526. The UI controller 104 has established secure connections, data and/or field mapping, links, settings or other connection between Pods 524 and 526 for the purpose of secure exchange of regulated data and performing one or more job functions while increasing compliance rate. The preconfigured Pod 502 can be called a lab order management or lab ordering Act. Additionally, the user of the UI 102 can open other preconfigured Acts 534, 536, 538 by clicking/double clicking on them and/or by dragging preconfigured Acts from a pre-configured Act Panel 530 and dropping them into an Act menu 532. Buttons 528 can be used to choose the type of a desired EMR application, type of a desired LOR form or other preconfigured Acts the user may request.

The application of the described embodiments is not limited to HIPAA or GDPR compliance; other industries that handle regulated data, such as finance, insurance, government audit offices and other data sensitive industries can also benefit from the described embodiments.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions.

The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

What is claimed is:

1. A computer-implemented method, the method comprising:
   receiving a first user request to access a first content and a first application capable of viewing, editing, and/or interacting with the first content;
   accessing the requested first application, wherein accessing comprises accessing an application engine of the first application and one or more libraries of the first application;
   generating an Act, comprising a multi-view display scene, capable of generating and viewing one or more content display blocks (Pods);
   within the Act, generating a first display Pod, comprising a first user interface for displaying the first application and the requested first content, wherein generating the first display Pod comprises modifying a user interface of the first application via the first application engine and the one or more libraries of the requested first application, wherein the modification comprises disabling and/or modifying regulation compromising features of the user interface of the requested first application, wherein the modified user interface comprises a regulation-compliant version of the user interface of the first application;

modifying the first application engine and/or the one or more libraries of the first application;

generating a regulation-compliant version of the first application, wherein the regulation-compliant version of the first application is configured to support the modified user interface of the first application;

displaying the modified user interface of the first application in the first display Pod;

accessing the requested first content;

displaying the requested first content, via the modified user interface in the first display Pod;

receiving a second user request to access a second content and a second application, the second application capable of viewing, editing and/or interacting with the second content, the second application comprising a second application engine and one or more libraries of the second application;

generating a regulation-compliant version of the second application, comprising modifying an application engine of the second application, modifying one or more libraries of the second application, and generating a modified user interface of the second application;

within the Act, generating a second display Pod corresponding to the second application;

within the Act, determining related content fields between the first display Pod and the second display Pod;

securely linking the related content fields between the first display Pod and the second display Pod, wherein both the first and second display Pods are simultaneously active and securely linked;

monitoring background processes of the first display Pod and the second display Pod;

detecting transfer of regulated data from the first content, and between the related content fields of the first and second display Pods; and securely executing the transfer of regulated data between the related content fields of the first and second display Pods, wherein the secure transfer comprises:

encrypting the regulated data from the first display Pod;

transferring the encrypted regulated data to a clipboard;

decrypting the regulated data;

transferring the decrypted regulated data to a related content field in the second display Pod; and directly injecting the regulated data from a related content field in the first display Pod to the related content field in the second display Pod, without copying, and pasting the regulated data into and/or from the clipboard.

2. The method of claim 1, wherein the regulation comprises one or more of Health Insurance Portability and Accountability Act (HIPAA) regulations to protect electronic Patient Health Information (ePHI), financial industry regulations, data privacy regulations and insurance industry regulations.

3. The method of claim 1, further comprising:

determining whether the accessed first application is compliant with the regulation by running a compliance audit script on the accessed first application, wherein the compliance audit script determines one or more of the following:

whether the accessed first application performs transport encryption, backup, authorization, storage encryption, maintains electronic Patient Health Information (ePHI) data integrity, when commanded, permanently disposes ePHI data and whether the accessed first application is stored on Health Insurance Portability and Accountability Act (HIPAA) compliant servers.

4. The method of claim 1, wherein the accessed first application comprises web browsers, webpages or applications running on webpages, word processors, spreadsheets, accounting applications, video or imaging applications, and/or PDF editors.

5. The method of claim 1 further comprising determining whether the accessed first application is compliant with the regulation and generating a visual and/or auditory alarm or warning when determining an accessed first application is non-compliant.

6. The method of claim 1 further comprising searching for regulated data in the requested first content, the accessed first application and/or servers where the accessed first application resides; and encrypting, and/or redacting, the regulated data, from the first display Pod, automatically or via receiving a user command.

7. The method of claim 1 further comprising:
receiving a request to store data from the first content;
determining a portion of data comprising regulated data;
encrypting the regulated data portion; and
storing the encrypted regulated data portion.

8. The method of claim 1 further comprising:
determining when the second application is a regulation non-compliant application;
determining an attempt of manual or automatic exchange of data comprising regulated data between the first display Pod and the second display Pod;
blocking the exchange;
displaying an auditory and/or visual warning message; and
cancelling the exchange, or removing the regulated data and
allowing the exchange.

9. The method of claim 1 further comprising;
determining an attempt to share regulated data based on first and/or second user requests;
determining scope of the regulated data to be shared in part based on one or more of the first and/or second user requests, a profile of the first and/or the second user, an access level and credentials of the first and/or second user, and/or a purpose of sharing the regulated data;
redacting or removing the regulated data outside the determined scope; and
sharing the regulated data within the determined scope.

10. The method of claim 1, further comprising determining whether the requested first application is regulation-compliant, based at least partly on, one or more of tables, lists, and libraries stored in a regulation compliance database.

11. The method of claim 1, wherein securely linking further comprises establishing a secured connection between the first and second applications, such that an automatic or manual exchange of data between the first and second applications are performed through the secured connection.

12. A non-transitory computer storage that stores executable program instructions that, when executed by one or more computing devices, configure the one or more computing devices to:

receive a first user request to access a first content and a first application capable of viewing, editing, and/or interacting with the first content;

access the requested first application, wherein accessing comprises accessing an application engine of the first application and one or more libraries of the first application;
generate an Act, comprising a multi-view display scene, capable of generating and viewing one or more content display blocks (Pods);
within the Act, generate a first display Pod, comprising a first user interface for displaying the first application and the requested first content,
wherein generating the first display Pod comprises modifying a user interface of the first application, via the first application engine and the one or more libraries of the requested first application,
wherein the modification comprises disabling and/or modifying regulation compromising features of the user interface of the requested first application, wherein the modified user interface comprises a regulation-compliant version of the user interface of the first application;
modify the first application engine and/or the one or more libraries of the first application;
generate a regulation-compliant version of the first application, wherein the regulation-compliant version of the first application is configured to support the modified user interface of the first application;
display the modified user interface of the first application in the first display Pod;
access the requested first content;
display the requested first content, via the modified user interface in the first display Pod;
receive a second user request to access a second content and a second application,
the second application capable of viewing, editing and/or interacting with the second content, the second application comprising a second application engine and one or more libraries of the second application;
generate a regulation-compliant version of the second application, comprising modifying an application engine of the second application, modifying one or more libraries of the second application, and
generating a modified user interface of the second application;
within the Act, generate a second display Pod corresponding to the second application;
within the Act, determine related content fields between the first display Pod and the second display Pod;
securely link the related content fields between the first display Pod and the second display Pod, wherein both the first and second display Pods are simultaneously active and securely linked;
monitor background processes of the first display Pod and the second display Pod;
detect transfer of regulated data from the first content, and between the related content fields of the first and second display Pods; and
securely execute the transfer of regulated data between the related content fields of the first and second display Pods, wherein the secure transfer comprises:
encrypting the regulated data from the first display Pod;
transferring the encrypted regulated data to a clipboard;
decrypting the regulated data;
transferring the decrypted regulated data to a related content field in the second display Pod; and
directly injecting the regulated data from a related content field in the first display Pod to the related content field in the second display Pod, without copying, and pasting the regulated data into and/or from the clipboard.

13. The non-transitory computer storage of claim 12, wherein the regulation comprises one or more of Health Insurance Portability and Accountability Act (HIPAA) regulations to protect electronic Patient Health Information (ePHI), financial industry regulations, data privacy regulations and insurance industry regulations.

14. The non-transitory computer storage of claim 12, further configured to: determine whether the accessed first application is compliant with the regulation by running a compliance audit script on the accessed first application, wherein the compliance audit script determines one or more of the following: whether the accessed first application performs transport encryption, backup, authorization, storage encryption, maintains electronic Patient Health Information (ePHI) data integrity, when commanded, permanently disposes ePHI data and whether the accessed first application is stored on Health Insurance Portability and Accountability Act (HIPAA) compliant servers.

15. The non-transitory computer storage of claim 12, wherein the accessed first application comprises web browsers, webpages or applications running on webpages, word processors, spreadsheets, accounting applications, video or imaging applications, and/or PDF editors.

16. The non-transitory computer storage of claim 12 further configured to determine whether the accessed first application is compliant with the regulation and generate a visual and/or auditory alarm or warning when determining an accessed first application is non-compliant.

17. The non-transitory computer storage of claim 12 further configured to:
search for regulated data in the requested first content, the accessed first application and/or servers where the accessed first application resides; and
encrypt, and/or redact, the regulated data, from the first display Pod, automatically or via receiving a user command.

18. The non-transitory computer storage of claim 12 further configured to:
receive a request to store data from the first content;
determine a portion of data comprising regulated data;
encrypt the regulated data portion; and
store the encrypted regulated data portion.

19. The non-transitory computer storage of claim 12 further configured to:
determine when the second application is a regulation non-compliant application;
determine an attempt of the manual or automatic exchange of data comprising regulated data between the first display Pod and the second display Pod;
block the exchange;
display an auditory and/or visual warning message; and
cancel the exchange, or remove the regulated data before allowing the exchange based at least partly on an input from the user.

20. The non-transitory computer storage of claim 12 further configured to:
determine an attempt to share regulated data based on first and/or second user requests;
determine scope of the regulated data to be shared in part based on one or more of the first and/or second user requests, an access level and credentials of the first and/or second user, and/or a purpose of sharing the regulated data;
redact or remove the regulated data outside the determined scope; and
share the regulated data within the determined scope.

21. The non-transitory computer storage of claim 12, further configured to: determine whether the requested first application is regulation-compliant, based at least partly on, one or more of tables, lists, and libraries stored in a regulation compliance database.

22. The non-transitory computer storage of claim 12, wherein the secure linking further comprises establishing a secured connection between the first and second applications, such that an automatic or manual exchange of data between the first and second applications are performed through the secured connection.

* * * * *